United States Patent
Meiri-Bendek et al.

(10) Patent No.: US 9,282,748 B2
(45) Date of Patent: Mar. 15, 2016

(54) HUMAN BREAST MILK LIPID MIMETIC AS A DIETARY SUPPLEMENT

(75) Inventors: Iris Meiri-Bendek, Shimshit (IL); Gai Ben Dror, Moshav Ofer (IL); Hala Laouz, Kfar Kana (IL); Dov Yaakobi, HaSolelim (IL); Zohar Bar-On, Karmiel (IL); Avidor Shulman, Kiryat Tivon (IL)

(73) Assignee: ENZYMOTEC LTD., Migdal Haemeq (IL)

( * ) Notice: Subject to any disclaimer, the term of this patent is extended or adjusted under 35 U.S.C. 154(b) by 1429 days.

(21) Appl. No.: 10/576,240

(22) PCT Filed: Oct. 21, 2004

(86) PCT No.: PCT/IL2004/000960
§ 371 (c)(1),
(2), (4) Date: Jan. 19, 2007

(87) PCT Pub. No.: WO2005/036987
PCT Pub. Date: Apr. 28, 2005

(65) Prior Publication Data
US 2007/0218169 A1 Sep. 20, 2007

(30) Foreign Application Priority Data
Oct. 22, 2003 (IL) .......................................... 158555

(51) Int. Cl.
| | |
|---|---|
| A21D 2/16 | (2006.01) |
| A23C 11/04 | (2006.01) |
| A23D 7/00 | (2006.01) |
| A23D 9/00 | (2006.01) |
| A23G 3/34 | (2006.01) |
| C11C 3/08 | (2006.01) |

(52) U.S. Cl.
CPC .............. *A21D 2/165* (2013.01); *A23C 11/04* (2013.01); *A23D 7/001* (2013.01); *A23D 9/00* (2013.01); *A23G 3/346* (2013.01); *C11C 3/08* (2013.01); *A23G 2200/08* (2013.01); *A23G 2200/12* (2013.01)

(58) Field of Classification Search
CPC ................................... A21D 2/165; C11C 3/00
See application file for complete search history.

(56) References Cited

U.S. PATENT DOCUMENTS

| | | | |
|---|---|---|---|
| 3,542,560 A | 11/1970 | Tomarelli | |
| 4,876,107 A | 10/1989 | King et al. | |
| 5,371,253 A * | 12/1994 | Cooper | 554/173 |
| 5,601,860 A | 2/1997 | Lien et al. | |
| 5,658,768 A | 8/1997 | Quinlan | |
| 5,709,888 A | 1/1998 | Gil et al. | |
| 6,248,909 B1 | 6/2001 | Akimoto et al. | |
| 6,292,792 B1 | 9/2001 | Baffes et al. | |
| 6,863,918 B2 | 3/2005 | Bindels et al. | |
| 8,618,050 B2 | 12/2013 | Shulman | |
| 2003/0072865 A1 | 4/2003 | Bindels et al. | |
| 2004/0137072 A1 | 7/2004 | Cockrum | |
| 2007/0218169 A1 | 9/2007 | Meiri Bendek | |
| 2008/0058415 A1 | 3/2008 | Shulman | |

FOREIGN PATENT DOCUMENTS

| | | |
|---|---|---|
| CA | 2357459 A1 | 10/2002 |
| CN | 1152856 A | 6/1997 |
| EP | 0 209 327 | 1/1987 |
| EP | 0209327 A2 | 1/1987 |
| EP | 376628 A2 * | 7/1990 |
| EP | 0 495 456 | 7/1992 |
| EP | 0496456 A1 | 7/1992 |
| EP | 0 882 797 | 12/1998 |
| EP | 0 965 578 | 12/1999 |
| EP | 1 062 873 | 12/2000 |
| EP | 1 252 824 | 10/2002 |
| WO | 9426854 | 11/1994 |
| WO | 9531110 A1 | 11/1995 |
| WO | WO95/31110 | 11/1995 |
| WO | WO 00/56869 | 9/2000 |
| WO | 00/58869 | 10/2000 |

OTHER PUBLICATIONS

Nutraingredients-usa.com article, published Jul. 2, 3003. (no author).*
Enzymotec information from enzymotec.com, pp. 5-7, retrieved Jun. 9, 2009. (no author).*
Carroll, Kenneth, K. "Upper Limits of Nutrients in Infant Formulas: Polyunsaturated Fatty acids and Trans Fatty Acids". 1989. Journal of Nutrition, 119:1810-1813.*
Susan E. Carlson, Ph.D. et al., Docosahexaenoic acid status of preterm infants at birth and following feeding with human milk or formula, Am. J. Clin. Nutr., 1986, pp. 798-804, v. 44, American Society for Clinical Nutrition.
Virgilio P. Carnielli, et al., Feeding premature newborn infants palmitic acid in amounts and stereoisomeric position similar to that of human milk: effects on fat and mineral balance, Am. J. Clin. Nutr., 1995, pp. 1037-1042, v. 61, American Society for Clinical Nutrition.
Virgilio P. Carnielli, et al., Structural Position and Amount of Palmitic Acid in Infant Formulas: Effects on Fat, Fatty Acid, and Mineral Balance, Journal of Pediatric Gastroenterology and Nutrition, Dec. 1996, pp. 553-560, v. 23(5).

(Continued)

*Primary Examiner* — Jenna A Watts
(74) *Attorney, Agent, or Firm* — Fleit Gibbons Gutman Bongini & Bianco PL; Paul D. Bianco; Katharine Davis

(57) ABSTRACT

The invention provides an enzymatically-prepared fat base composition which comprises a mixture of vegetable-derived triglycerides. The fat base composition has a total palmitic acid residues content of at most 38% of the total fatty acid residues, and at least 60%, preferably 62% of the fatty acid moieties at the sn-2 position of the glycerol backbone are palmitic acid residues, at least 70% of the fatty acid moieties at the sn-1 and sn-3 positions of the glycerol backbone are unsaturated, at least 40%, preferably 40-60%, of the unsaturated fatty acid moieties at the sn-1 and sn-3 positions are oleic acid moieties, and at least 6%, preferably 6-17%, of the unsaturated fatty acid moieties at the sn-1 and sn-3 positions are linoleic acid moieties. The invention also provides preparation and various uses of the fat base composition in the field of infant nutrition.

8 Claims, No Drawings

(56) References Cited

OTHER PUBLICATIONS

J. E. Chappell, B. A. SC., et al., Fatty acid balance studies in premature infants fed human milk or formula: Effect of calcium supplementation, Fetal and Neonatal Medicine, The Journal of Pediatrics, Mar. 1986, pp. 439-447, v. 108, n. 3.

L. J. Filer, Jr., et al., Triglyceride Configuration and Fat Absorption by the Human Infant, J. Nutrition, pp. 293-298, v. 99.

Margit Hamosh, Ph. D., Lingual and Gastric Lipases, Nutrition, Nov./Dec. 1990, pp. 421-428, v. 6, n. 6.

Fikri M. Hanna. M. D., et al., Calcium-Fatty Acid Absorption in Term Infants Fed Human Milk and Prepared Formulas Simulating Human Milk, Pediatrics, Feb. 1970, pp. 216-224, v.45, n. 2.

Olle Hernell, et al., Digestion and Absorption of Human Milk Lipids, Perinatal Nutrition, Academic Press., 1988, pp. 259-272.

Sheila M. Innis, et al., Plasma and red blood cell fatty acids of low-birth-weight infants fed their mother's expressed breast milk or preterm-infant formula, Am. J. Clin. Nutr., 1990, pp. 994-1000, v. 51, American Socierty for Clinical Nutrition.

Sheila M. Innis, PH. D., et al., Effects of Developmental Changes and Early Nutrition on Cholesterol Metabolism in Infancy: A Review, Journal of the American College of Nutrition, 1992, pp. 63S-68S., v. 11. n. 2.

Sheila M. Innis, et al., Saturated fatty acid chain length and positional distribution in infant formula: effects on growth and plasma lipids and ketones in piglets, Am. J. Clin. Nutr., 1993, pp. 382-390, v. 57, American Socierty for Clinical Nutrition.

Sheila M. Innis, et al., Evidence That Palmitic Acid is Absorbed as sn-2 Monoacylglycerol from Human Milk by Breast-Fed Infants, 1994, Lipids, pp. 541-545, v. 29, n. 8.

Sheila M. Innis, et al., Palmitic Acid is Absorbed as sn-2 Monopalmitin from Milk and Formula with Rearranged Triacylglycerols and Results in Increased Plasma Triglyceride sn-2 and Cholesteryl Ester Palmitate in Piglets, Nutrient Metabolism, J. Nutr., 1995, pp. 73-81, v. 125, American Institute of Nutrition.

Christine Jensen, MS, RD, et al., Absorption of individual fatty acids from long chain or medium chain triglycerides in very small infants, The American Journal of Clinical Nutrition, May 1986, pp. 745-751, v. 43, American Society for Clinical Nutrition.

B. Koletzko, et al., Effects of dietary long-chain polyunsaturated fatty acids on the essential fatty acid status of premature infants, European Journal of Pediatrics, 1989, pp. 669-675, v. 148.

Eric L. Lien, et al., The Effect of Triglyceride Positional Distribution on Fatty Acid Absorption in Rats, Journal of Pediatric Gastroenterology and Nutrition, Aug. 1997, pp. 167-174, v. 25(2).

A. Lopez-Lopez, et al., The influence of dietary palmitic acid triacylglyceride position on the fatty acid, calcium and magnesium contents of at term newborn faeces, Early Human Development, 2001, pp. S83-S94, v. 65 Suppl., www.elsevier.com/locate/earlhumdev.

A. Lucas, et al., Randomised controlled trial of a synthetic triglyceride milk formula for preterm infants, Original Articles, Archives of Diseases in Childhood, 1997, pp. F178-F184, v.77.

F. H. Mattson, et al., The Specificity of Pancreatic Lipase for the Primary Hydroxyl Groups of Glycerides, J. Biol. Chem., pp. 735-740, v. 219, 1956.

Steven E. Nelson, et al., Palm olein in infant formula: absorption of fat and minerals by normal infants, Am. J. Clin. Nutri., 1996, pp. 291-296, v. 64, American Society for Clinical Nutrition.

Steven E. Nelson, BA, et al., Absorption of Fat and Calcium by Infants Fed a Milk-Based Formula Containing Palm Olein, Journal of the American College of Nutrition, 1998, pp. 327-332, v. 17, n. 4.

Karin M. Ostrom, Ph. D., et al., Lower Calcium Absorption in Infants Fed Casein Hydrolysate- and Soy Protein-Based Infant Formulas Containing Palm Olein Versus Formulas without Palm Olein, Journal of the American College of Nutrition, 2002, pp. 564-569, v. 21, n. 6.

Jane C. Putman, M. S., et al., The effect of variations in dietary fatty acids on the fatty acid composition of erythrocyte phosphatidylcholine and phosphatidylethanolamine in human infants, The American Journal of Clinical Nutrition, Jul. 1982, pp. 106-114, v. 36.

P. T. Quinlan, et al., The Relationship between Stool Hardness and Stool Composition in Breast- and Formula-Fed Infants, Journal of Pediatric Gastroenterology and Nutrition, 1995, pp. 81-90, v. 20.

Donald M. Small, The Effects of Glyceride Structure on Absorption and Metabolism, Annual Rev. Nutr., 1991, pp. 413-434, v. 11.

R. M. Tomarelli, et al., Effect of Positional Distribution on the Absorption of the Fatty Acids of Human Milk and Infant Formulas, J. Nutrition, 1968, pp. 583-590, v. 95.

J. P. Van Biervliet, et al., Plasma Apoprotein and Lipid Patterns in Newborns: Influence of Nutritional Factors, Acta Paediatr. Scand., 1981, pp. 851-856, v. 70.

Chi-Sun Wang, et al., Studies on the Substrate Specificity of Purified Human Milk Bile Salt-activated Lipase, The Journal of Biological Chemistry, Aug. 10, 1983, pp. 9197-9202, v. 258, n. 15.

Elsie M. Widdowson, et al., Body Fat of British and Dutch Infants, British Medical Journal, Mar. 22, 1975, pp. 653-655, v.1.

Database Medline/NLM Online, Nov. 15, 1997, Cadogan J. et al., "Milk intake and bone mineral acquisition in adolescent girls: randomised, controlled intervention trial", XP002315046, database access No. NLM9390050, British Medical Journal, v. 315, pp. 1255-1260.

Database Medline/NLM Online, USNLM, XP002315047, database access No. NLM14520257, Oct. 2003, Volek, Jeff S. et al.: "Increasing fluid milk favorably affects bone mineral density responses to resistance training in adolescent boys", Journal of the American Dietetic Assoc, vol. 103, pp. 1353-1356.

Database Embase/Elsevier Online, Elsevier Science Pub., XP002315048, database access No. EMB-2000369954, 2000, Gueguen L.: "Calcium balance: Requirements, intake and bioavailability", Nutrition Clinique et Metabolisme.

Database Embase/Elsevier Online, Elservier Science Pub., XP002315049, Database access No. EMB-2003380690, Sep. 1, 2003, Scholz-Ahrens K.E.: "Nutrients of milk and their relevance for health", Medizinische Welt, v. 54, n. 9, pp. 222-230.

Database FSTA/IFIS Online, XP002315600, Database access No. 96-1-08-n0030, World of Ingredients, Mar./Apr. 1996, Anonymous: "Betapol, a breakthrough in infant formula fats".

"Enzymotec launches InFat-perfect fat for infant formulas", Online, Jul. 4, 2003, XP002315599, Retrieved from Internet URL: www.foodingredientsfirst.com/newsmaker.

Database Biosis Online, Biosciences Info. Service, XP002315050, Database access No. PREV199799383168, 1996, Carnielli Virgilio P. et al.: "Structural position and amount of palmitic acid in infant formulas: Effects on fat, fatty acid, and mineral balance", J. of Ped. Gastro. & Nutrition, v. 23, n. 5, pp. 553-560.

Database FSTA/IFIS Online, XP002315051, Database access No. 2000-00-g0249, FSTA, 1999, Kennedy K. et al.: "Double-blind, randomized trial of a synthetic tricylglycerol in formula-fed term infants: effects on stool biochemistry, stool characteristics, and bone mineralization", Am. J. of Clinical Nutrition, v. 70(5), pp. 920-927.

Database Embase/Elsevier Online, Elsevier Science Pub., XP002315052, Database access No. EMB-1979225226, Jenness R.: "The composition of human milk", Seminars in Perinatology, 1979.

Database Medline/NLM, USNLM, XP002315783, access No. NLM9462186, Nov. 1997, Lucas A. et al.: "Randomised controlled trial of a synthetic triglyceride milk formula for preterm infants", Archives of Disease in Childhood, Fetal and Neonatal edition, v. 77, n. 3, pp. F178-F184.

R. Jacobsen, et al., Effect of short-term high dietary calcium intake on 24-h energy expenditure, fat oxidation, and fecal fat excretion, International Journal of Obesity, 2005, pp. 292-301, v. 29.

Robert G. Jensen, Invited Review: The Composition of Bovine Milk Lipids: Jan. 1995 to Dec. 2000, J. Dairy Sci., pp. 295-350, v. 85.

http://www.umm.edu/home>medical reference>alternative/complementarymedicine>Tableofcontents>depletions>Antacids AluminumCalciumandMagnediumContainingPreparationscl.htm, Univ. of Maryland Medical Center Website.

International Search Report for PCT/IL04/00960.

International Preliminary Report on Patentability PCT/IL04/000960.

"Betapol" World of Ingredients, 1996, pp. 41-42, XP009043320.

Written Opinion for PCT/IL2004/000960 filed Oct. 21, 2004.

(56) References Cited

OTHER PUBLICATIONS

Kathy Kennedy et al., Double-blind, randomized trial of a synthetic triacylglycerol in formula-fed term infants: effects on stool biochemistry, stool characteristics, and bone mineralization, The American Journal of Clinical Nutrition, 1999, pp. 920-927, vol. 70.
A. Lucas et al., Randomised controlled trial of a synthetic triglyceride milk formula for preterm infants, Archives of Disease in Childhood, 1997, pp. F178-F184, vol. 77.
International Search Report for PCT/IL2004/000961 filed Oct. 21, 2004 (Claims same priority as U.S. Appl. No. 10/576,240).
Jane C. Putnam, et al., the effect of variations in dietary fatty acid on the fatty acid composition of erythrocyte phosphatidylethanolamine in human infants, The American Journal of Clinical Nutrition, Jul. 1982, pp. 106-114 v. 36.
IPER—International Preliminary Report on Patentability PCT/IL04/00961, published on Apr. 22, 2006.
Copending U.S. Appl. No. 10/576,239, Preliminary Amendment and related papers Feb. 5, 2007.
Copending U.S. Appl. No. 10/576,239, Requirement for Restriction Mar. 16, 2009.
Copending U.S. Appl. No. 10/576,239, Response to Office Action Mar. 16, 2009.
Copending U.S. Appl. No. 10/576,239, Non-Final Rejection Jul. 15, 2009.
Copending U.S. Appl. No. 10/576,239, Response to Office Action Oct. 14, 2009.
Copending U.S. Appl. No. 10/576,239, Final Rejection Jan. 5, 2010.
Copending U.S. Appl. No. 10/576,239, Response to Office Action May 5, 2010.
Copending U.S. Appl. No. 10/576,239, Office Action Jul. 7, 2010.
Copending U.S. Appl. No. 10/576,239, Response to Office Action and Request for Continued Examination Dec. 7, 2010.
Copending U.S. Appl. No. 10/576,239, Notice of Noncompliant Amendment Jan. 18, 2011.
Betapol, World of Ingredients, 1996, p. 41-42, abstract XP002315600.
Spurgon et al., An Investigation of the general reproductive and postnatal developmental toxicity of Baetapol, a human milk fat equivalent, available online Aug. 2, 2003.
WO—Written Opinion for PCT/IL2004/000961, published on Apr. 22, 2006.
Copending U.S. Appl. No. 10/576,239, Response to Office Communication Feb. 16, 2011.
InFat TM 3070 Certificated of Analysis Manufactured 2006-2008.
Zock, P.L. et al, Partial conservation of the sn-2 position of dietary triglycerides in fasting plasma lipids in humans, European Journal of Clinical Investigation (1996) 26, 141-150.
Haumann, Barbara Fitch, Strucured lipids allow fat, INFORM, vol. 8, No. 10, Oct. 1997.
http://www.umm.edu/home>medical reference>alternative/complimentarymedicine>tableofcontents>depletions>antacids aluminumcalciummagnediumcontainingpreparationscl.htm, Univ. of Maryland Medical Center Website.
Nutraingredients-usa.com article, published Jul. 2, 2003. (no author).
Enzymoted information from enyzmotec.com, p. 5-7, retrieved Jun. 9, 2009.
Innis, Sheila M. et al, Structured Triacylglycerols in Infant Nutrition and Metabolism, 1998 by AOCS Press, Department of Paediatrics.
Denke, Margo A. et al, Short-Term Dietary Calcium Fortification Increases Fecal Saturated Fat Content and Reduces Serum Lipids in Men, 1993, American Journal of Nutrition 123:1047-1053.

Chappell, J.E., Fatty acid balance studies in premature infants fed human milk or formula: Effect of calcium supplementation, 1986; 108:439-447, Fetal and Neonatal Medicine.
International Preliminary Report on Patentability PCT/IL04/00960 dated Dec. 21, 2005.
Written Opinion for PCT/IL2004/000960 received Feb. 22, 2005.
A. Lucas et al., Randomized controlled trial of a synthetic triglyceride milk formula for preterm infants, Archives of Disease in Childhood, 1997, pp. F178-F184, vol. 77.
www.PreparedFoods.com, Nov. 1999.
XP-002315599, Jul. 4, 2003, Food Ingredients First.com.
Kennedy, Kathy et al, Double-blind, randomized trial of a synthetic triacylglycerol in formula-fed term infants: effects on stool biochemistry, stool characteristics, and bone mineralization 1-3, pp. 920, 1999, The American Journal of Clinical Nutrition.
Carnielli, Virgilio P et al, Feeding premature newborn infants palmitic acid in amounts and stereoisomeric position similar to that of human milk: effects on fat and mineral balance 1-3, Jul. 21, 2010, pp. 1037, The American Journal of Clinical Nutricial.
Carnielli, Virgilio P et al, Structural Position and Amount of Palmitric Acid in Infant Formulas: Effects on Fat, Fatty Acid, and Mineral Balance, Journal of Pediatric Gastroenterology & Nutrition: Dec. 1996—vol. 23—Issue 5—pp. 553-560.
Wells, John, Infant and follow-on formulas: the next decade, Jul. 21, 2010, BNF Nutrition Bulletin, vol. 23.
Quinlan P., Structuring Fats for Incorporation into Infant Formulas, Jul. 21, 2010, Fats in Infant Formulas.
Zampelas A. et al, The effect of triacylglycerol fatty acid positional distribution on postprandial plasma metabolite and hormone responses in normal adult men, British Journal of Nutrition (1994) 71, 401-410.
Martin, JC et al, Triacylglycerol structure of human colostrum and mature milk, Lipids, Jul. 1993, 28(7): 637-43.
Kavanagh, A.R. A breakthrough in infant formula fats, 1997, vol. 4, No. 3.
Office action dated May 22, 2012 for U.S. Appl. No. 10/576,239.
A. Zampelas, et al, Effect of triacylglycerol fatth acid . . . , British Journal of Nutrition (1994), 71, p. 401-410.
Response to election/restriction requirement for U.S. Appl. No. 10/576,239 dated May 13, 2009.
Kurvinen et al, "Molecular Weight Distribution and Regioisomeric Structure of Triacylglycerols in Some Common Human Milk Substitutes", JAOCS, vol. 79, No. 1, 2002, pp. 13 to 22.
Innis et al, "Saturated fatty acid chain length and positional distribution in infants formuls: effects on grown and plasma lipids and ketones in piglets1-3", Am J. Clin Nutr. 1993, vol. 57, pp. 382-390.
Carnielli et al, "Effect of dietary triacylglycrol fatty acid positional distribution on plasma lipid classes and their fatty acid composition in preterm infants1-3", J. Clin Nutr. 1995, vol. 62, pp. 776-781.
Submission to US FDA for GRAS Exemption Claim for Betapol dated May 28, 2003, GRN No. 131, available at http://www.accessdata.fda.gov/scripts/fcn/gras_notices/309841A.PDF.
Croklaan, Notice of opposition to a European U.S. Pat. No. 1,681,945. Dec. 2011.
Zock, P.L, et al., "Partial conservation of the sn-2 position of dietary triglycerides in fasting plasma lipids in humans", European Journal of Clinical Investigation, 1996, pp. 141-150, 26, Blackwell Science Ltd.
Office Action (OA) mailed May 9, 2013 for U.S. Appl. No. 10/576,239.
For U.S. Appl. No. 10/576,239 Response to Office Action dated Jul. 9, 2013, Notice of Allowance and Interview Summary dated Aug. 13, 2013.

\* cited by examiner

HUMAN BREAST MILK LIPID MIMETIC AS A DIETARY SUPPLEMENT

FIELD OF THE INVENTION

The present invention refers to the field of infant nutritional foods. More specifically, the present invention describes novel fat compositions which are components in the preparation of fat blends and infant formulas, as well as the process of producing the same.

BACKGROUND OF THE INVENTION

All publications mentioned throughout this application are fully incorporated herein by reference, including all references cited therein.

Lipids in general are the building blocks of life. They are used as building blocks of membranes, cells and tissues, as energy sources, either immediate or stored, as precursors to a variety of other bio-molecules, as well as biochemical signals. In at biochemical processes lipids have an important role.

Many lipids, and especially triglycerides, are consumed in the human nutrition on a daily basis. In most cases, these lipids are metabolized and used for energy storage, precursors for biosynthesis of other lipids or bio-molecules. Whatever the fate of the lipids in the metabolic pathways, during and after their consumption, they interact with other nutrients or their metabolic products.

In human milk, and in most infant formulas, about 50% of the dietary calories are supplied to newborns as fat. More than 98% of this milk fat is in the form of triglycerides, which contain saturated and unsaturated fatty acids esterified to glycerol.

Fatty acids in human milk fat have a highly specific positional distribution on the glycerol backbone. This specific configuration is known to have a major contribution to the efficiency of nutrient absorption.

Palmitic acid (C16:0) is the predominant saturated fatty acid, constituting 20-25% of the fatty acids in mature human milk. 70-75% of this fatty acid are esterified at the sn-2 position of the triglycerides. In contrast, palmitic acid present in vegetable oils, which are most commonly used in the manufacture of infant formulas, is esterified at the sn-1 and sn-3 positions, while the sn-2 position is predominantly occupied by unsaturated fatty acids.

Triglyceride Digestion by the Infant

The triglyceride digestive process of the neonate is complex. It is initiated by a gastric phase catalyzed by gastric or lingual lipase [Hamosh M. (1990) Nutrition; 6:421-8]. This initial lipolysis allows maximal activity of pancreatic colipase-dependent lipase during the intestinal phase of digestion. The pancreatic lipase system attacks the triglyceride with a high degree of positional specificity. Lipolysis occurs predominantly at the sn-1 and sn-3 positions, yielding two free fatty acids and a 2-monoglyceride [Mattson F H. & Beck L H. (1956) J. Biol. Chem.; 219:735-740]. Monoglycerides are well absorbed independent of their constituent fatty acid. In contrast, the absorption of free fatty acids varies greatly, depending on their chemical structure. Mono and polyunsaturated fatty acids are well absorbed, as are saturated fatty acids of 12 carbons or less in chain length. The coefficient of absorption of free long chain saturated fatty acids i.e. palmitic acid is relatively low [Jensen C, et al. (1988) Am. J. Clin. Nutr.; 43:745-51], due in part to a melting point above body temperature (~63°) and the tendency of these fatty acids to form hydrated fatty acid soaps with minerals such as calcium or magnesium at the pH of the intestine [Small D M. (1991) Annu. Rev. Nutr.; 11:413-434].

Several studies have demonstrated the preferential absorption of palmitic acid when present at the triglyceride sn-2 position [Lien E L. et al. (1997) J. Ped. Gastr. Nutr.; 52(2): 167-174; Carnielli V P. et al. (1995) Am. J. Clin. Nutr.; 61:1037-1042; Innis S M. et al. (1993) Am. J. Clin. Nutr.; 57:382-390; Filer L. J. et al. (1969) J. Nutr.; 99:293-8]. Studies comparing the palmitic acid absorption of human milk and formulas conclude that the absorption of palmitic acid is higher in human milk [Chappel J E. et al. (1986) J. Pediatr.; 108:439-447; Hanna F M. et al. (1970) Pediatr.; 45:216-224; Tommarelli R M, et al. (1968) J. Nutr.; 95:583-90]. The greater absorption of fat and calcium in breast-fed infants compared with those fed formula has been ascribed to two factors: the presence in breast milk of a lipolytic enzyme (the bile salt-stimulated lipase) and the relatively high proportion of palmitic acid at the sn-2 position of the triglyceride [Hernell O. et al. (1988) Periniatal Nutrition. New York: Academic Press.; 259-272; Wang C S. et al. (1983) J. Biol. Chem.; 258:9197-9202]. Higher palmitic acid absorption was obtained with formulas rich in palmitic acid esterified in the sn-2 position of the triglycerides, than with those containing palmitic acid predominantly esterified in the sn-1,3 positions [López-López A. et al. (2001) Early Hum. Dev.; 65:S83-S94].

A study comparing the absorption of fat and calcium by infants fed a formula containing a blend of palm olein and soy oil (high levels of palmitic acid at the sn-1,3 positions) and a formula containing a blend of soy oil and coconut oil (low levels of palmitic acid) showed that the mixture of palm olein and soy oil, although providing the proportion of palmitic and oleic acids similar to those of human milk fat, was less absorbed [Nelson S E. et al. (1996) Am. J. Clin. Nutr.; 64:291-296]. Another study showed that fat absorption in infants fed formula containing lard was reduced when the high proportion of sn-2 palmitin in lard was reduced to 33% by chemical randomization [Filer (1969) id ibid.].

The composition of monoglycerides absorbed from the intestinal lumen is important to the fatty acid distribution of circulating lipids because about 70% of the fatty acids absorbed as sn-2 monoglycerides are conserved in the original position during re-esterification to form triglycerides in the intestinal cells [Small (1991) id ibid.].

Studies in piglets provided evidence that palmitic acid, when absorbed from milk or formula with rearranged triglycerides as a sn-2 monoglyceride, is conserved through the process of triglyceride reassembly in the enterocyte and secretion in plasma lipoprotein triglycerides [Innis S M. et al. (1995) J. Nutr.; 125:73-81]. It has also been shown that the distribution of saturated fatty acids in human milk and infant formula is a determinant of the fatty acid distribution of infant plasma triglycerides and phospholipids [Innis S M. et al. (1994) Lipids.; 29:541-545].

During the first year of life an infant's birth weight triples and the length is increased by 50%. To meet the requirements of their rapidly expanding skeletal mass, growing infants require a bioavailable source of calcium. For formula-fed infants, availability of calcium depends on the composition of the formula [Ostrom K. M. et al. (2002) J. Am. Coll. Nutr.; 21(6):564-569].

As mentioned above, the digestion of triglycerides involves lipolysis at the sn-1 and 3 positions and formation of free fatty acids and 2-monoglycerides. When palmitic acid is located at the sn-1,3 positions, as is the case in most infant formulas, it is released as free fatty acid which tends to form insoluble calcium soaps. In contrast, palmitic acid esterified to the sn-2 position, as in human milk, is unavailable to form calcium soaps [Small (1991) id ibid.].

Several studies have shown a correlation between formulas containing high levels of palmitic acid situated at the sn-1,3 positions of the triglyceride and reduction in calcium absorption [Nelson S E. et al. (1998) *J. Amer. Coll. Nutr.;* 17:327-332; Lucas A. et al. (1997) *Arch. Dis. Child.;* 77:F178-F187; Carnielli V P. et al. (1996) *J. Pediatr. Gastroenterol. Nutr.* 23:553-560; Ostrom (2002) id ibid.; Hanna (1970) id ibid.]. In addition, it was shown that dietary triglycerides containing palmitic acid predominantly at the sn-2 position, as in human milk, have significant beneficial effects on the intestinal absorption of fat and calcium in healthy term infants as well as in preterm infants [Carnielli (1996) id ibid.; Carnielli (1995) id ibid.; Lucas (1997) id ibid.]. Infants fed a formula containing high levels of palmitic acid at the sn-1,3 positions showed greater fecal excursion of calcium and, hence, a lower percentage absorption of calcium compared to infants fed a formula containing low levels of palmitic acid [Nelson (1996) id ibid.]. Fecal excretion of calcium was closely related to the fecal excretion of fat. This study also showed that urinary phosphorus excretion increased and phosphorus retention decreased when infants were fed the formula containing high levels of palmitic acid at the sn-1,3 positions. These findings presumably reflect lower availability of calcium for deposition in bones.

Another important issue which is associated with formula feeding is constipation in both term and preterm infants which, in the latter, can lead to life threatening complications. By contrast, constipation is rare in breast fed term infants. A study comparing breast fed and formula fed infant stool hardness and composition showed that calcium fatty acid soaps are positively correlated to stool hardness. Stools from formula-fed infants were significantly harder than those of the breast-fed infants suggesting different handling of saturated fatty acids [Quinlan P T. et al. (1995) *J. Pediatr. Gastr. and Nutr.;* 20:81-90].

In an attempt to overcome the decreased calcium absorption and hard stool phenomena, infant formula manufacturers tend to deviate from the fatty acid profile by replacing palmitic acid with lauric acid and, in some cases, by increasing the polyunsaturated fatty acid content. Studies have shown that fatty acid composition of the diet influences the fatty acid composition of developing infant tissue [Widdowson E. M. (1975) *Br. Med. J.;* 1:633-5; Carlson S E. et al. (1986) *Am. J. Clin. Nutr.;* 44:798-804; Innis S M. et al. (1990) *Am. J. Clin. Nutr.;* 5:994-1000; Koletzko B. et al. (1989) *Eur. J. Pediatr.;* 148:669-75] and thus the lipoprotein and lipid metabolism differ between breast-fed and formula-fed infants [Putnam J. C. et al. (1982) *Am. J. Chin. Nutr.;* 36:106-114; Innis S M. et al. (1992) *Am. Coll. Nutr.;* 11:63S-8S; Van Biervliet J P. et al. (1981) *Acta. Paediatr. Scand.;* 70:851-6].

Innis and colleagues [Innis (1993) id ibid.], when comparing three formulas containing similar amounts of saturated fatty acids—C8-C14, C16 from palm oil predominantly in the sn-1,3 positions), or C16 from synthesized triglyceride predominantly in the sn-2 position)—showed that the chain length of saturated fatty acids in infant formula influences the metabolism of the dietary oleic, linoleic and alpha-linolenic acids. This study also showed that the sn-2 configuration of C16 in human milk triglycerides seems to have unique properties that extend beyond absorption. These include effects on HDL and cholesterol concentrations, and the cholesterol ester fatty acid composition.

The impact of soap formation on calcium absorption can be significant. Many infant formulas contain sufficient saturated fatty acids to form soaps with virtually all the calcium available.

U.S. Pat. No. 4,876,107 (corresponding to EP 0 209 327) describes a substitute milk fat composition which is suitable as replacement fat in infant formulations. In this fat composition the total palmitic acid residues present is as high as 45%, with at least half of the fatty acid residues at the 2-position of the glycerol backbone being palmitic. The product has about 27% palmitic acid residues at the 1- and 3-positions, and the other substituents at the 1- and 3-positions are mainly unsaturated $C_{16}$ and C18 fatty acid moieties. The fat composition is prepared by a specific process, in the presence of Hexane. Rather high levels of the fat compositions are required for the preparation of final infant formulations.

EP 0 496 456 also discloses substitute milk fat compositions. These compositions have a saturated fatty acid content at the sn-2 position of at least 40%, most of which are palmitic acid residues, and contain 0.2-7% linolenic acid moieties, 70% of which are bonded at the 1- and 3-positions of the glycerol moieties, the remaining acid moieties at the 1- and 3-positions, other than unsaturated fatty acids, are saturated $C_4$-$C_{12}$ fatty acids.

U.S. Pat. No. 5,658,768 discloses a multiple-step process for preparing triglyceride compositions in which more than 40% of the saturated fatty acid moieties are at the 2-position. Many of the steps involve enzymatic modifications.

In sum, one of the most pronounced differences between mother's milk and infant formulas is in the fat composition. In mother's milk, most of the saturated fatty acids (about 70%, mainly palmitic acid) are located at the sn-2 position of the triglycerides while the sn-1,3 positions are mainly occupied with unsaturated fatty acids. However, most infant formulas do not contain such composition and the result is the loss of energy (in the form of palmitic acid) and calcium by the infants. The reason for that is first and foremost, the limited availability of a fat mimicking the human breast milk fat. Currently, there is yet no natural alternative from a safe vegetal source. Limited sources are those of animal origin, which are extremely non-safe in a most delicate field like infant nutrition. One alternative in the past was to use lard, however health risks related to porcine viruses that can be transmitted to infants have caused this fat source to be eliminated. While there exist commercially available fats which mimic the fat composition of human breast milk, such as those described, e.g. in EP 0 209 327, they suffer several major drawbacks, inter alia the following:

Good blends are of very high cost and apparently limited availability, due to inferior methods of production. This is even more pronounced if the blends are to be used together with other new and relatively costly important nutrients, such as long-chain polyunsaturated fatty acid (LC-PUFA);

Commercial versions available on the market are inferior in terms of health benefits (only 43% of the total palmitic acid residues are esterified at the sn-2 position). A ratio of less than 50% (of the total palmitic acid is esterified at the sn-2 position) may have no meaningful benefits in terms of calcium and energy intake.

Production is by using a genetically modified enzyme, hence the product may be considered as GMO with the risks involved.

The products have to be incorporated to the formula blends at relatively high quantities, which may leave little room for any additional important oils and lipids to be incorporated without raising the total fat content of the formula.

Therefore, there are three important points when it comes to the triglyceride composition of human milk fat replacement:
1) The total amount of palmitic acid;
2) The ratio of palmitic acid at the sn-2 position (expressed as percent of palmitic acid at the sn-2 position from the total palmitic acid level);
3) The amount of oleic acid.

The amount of oleic acid is important in order to preserve the calcium and energy for the infant, and ensure normal and healthy development, since the fatty acids at the sn-1,3 positions of the oil component should be unsaturated. The higher the amount of unsaturated fatty acids, such as oleic acid, the better, since this indicates that most of the sn-1,3 positions are occupied by fatty acids that will not create harmful complexes with calcium. Consequently, the infant will not lose either energy (in the form of fatty acids) or calcium.

In order to find an optimal infant formula, wherein the amounts and composition of the fats are as close as possible to mother's milk, which would also be cost-effective, the present inventors have developed a new fat-based preparation in which the amount of palmitic acid residues at the sn-2 position of the triglycerides, and the amount of oleic acid are as close as possible to the optimum desired, as described below.

Thus, it is an object of the present invention to provide compositions typically comprising the fatty acids palmitic, oleic, linoleic and stearic acid, wherein up to 70% of the palmitic acid present is located in the sn-2 position. The invention also provides the process for preparation of said composition. Other uses and objects of the invention will become clear as the description proceeds.

SUMMARY OF THE INVENTION

The present invention relates to an enzymatically prepared fat base composition comprising a mixture of vegetable-derived triglycerides, characterized in that it has a total palmitic acid residues content of at most 38% of the total fatty acid residues, and in that at least 60%, preferably 62% of the fatty acid moieties at the sn-2 position of the glycerol backbone are palmitic acid residues.

In the fat base composition of the invention, preferably at least 70% of the fatty acid moieties at the sn-1 and sn-3 positions of the glycerol backbone are unsaturated. More preferably, at least 40%, preferably 40-60%, of the unsaturated fatty acid moieties at the sin-1 and sn-3 positions are oleic acid moieties. Particularly, at least 6%, preferably 6-17%, of said unsaturated fatty acid moieties at the sn-1 and sn-3 positions are linoleic acid moieties.

The invention further relates to a substitute human milk fat composition comprising a blend of at least 25% of the fat base composition of any one of claims 1 to 5 with up to 75% of at least one vegetable oil.

The vegetable oil may be selected from the group comprising soy oil, palm tree oil, canola oil, coconut oil, palm kernel oil, sunflower oil, corn oil and rapeseed oil.

In a further aspect, the invention relates to an infant formula comprising the substitute human milk fat composition of the invention. The infant formula of the invention may optionally further comprise vitamins, minerals, nucleotides, amino acids and carbohydrates.

In yet another embodiment, the invention relates to a process for the preparation of the fat base composition of the invention, comprising essentially the steps of reacting a palmitic acid rich oil with unsaturated fatty acids, preferably oleic acid, in the presence of an insoluble catalyst; removing the catalyst; distilling the excess free fatty acids; bleaching the oil; and optionally deodorization of the resulting product. The process of the invention may optionally further comprise a step of fractionation before the deodorization step.

Still further, the invention relates to a process for the preparation of the substitute human milk fat composition of the invention, comprising admixing said vegetable oil with the fat base composition of the invention.

Also encompassed are the use of the fat base composition of the invention in the preparation of a substitute human milk fat composition for infant formulae, and its use in the preparation of an infant formula.

DETAILED DESCRIPTION OF THE INVENTION

In an attempt to provide the best and closest to the mother's human milk fat substitute, the present inventors have generated novel fat compositions in which the amounts and positions of saturated and unsaturated fatty acids have been manipulated so as to achieve that goal.

The terms "fat" and "lipid" are used herein interchangeably.

Lipids, under the scope of this invention, include triglycerides and derivatives, such as mono- and di-glycerides.

Preferably, the lipid constituent of the dietary ingredient of the invention is based on a synthetic oil (which can be produced both chemically and, preferably, enzymatically) which mimics the triglyceride composition of human breast milk fat. This oil has, preferably, a high level of palmitic acid at the sn-2 position of the triglycerides, consisting of above 40%, and preferably over 60%, more preferably over 65% of the total palmitic acid content. Furthermore, this oil has a high level of unsaturated fatty acids at Sn1 positions 1 and 3, preferably over 50%. This ingredient is also referred to herein as InFat™ (Enzymotec Ltd., Migdal HaEmeq, Israel).

Thus, in a preferred embodiment, the present invention provides an enzymatically prepared fat base composition comprising a mixture of vegetable-derived triglycerides, characterized in that:
the total palmitic acid residues content is at most 38% of the total fatty acid residues;
at least 60% of the fatty acid moieties at the sn-2 position of the glycerol backbone are palmitic acid residues.

InFat is an advanced fat-base ingredient for the production of fat preparations used in infant nutrition formulas. It is an exclusive fat-base, designed and manufactured with specific triglycerides composition and structure.

The essential features of the fat-base composition are as follows:
at least 62% of the total palmitic acid residues are at the sn-2 position of the glycerol backbone;
at least 70% of the fatty acid moieties at the sn-1 and sn-3 positions of the glycerol backbone are unsaturated;
at least 40%, preferably 40-60%, of said unsaturated fatty acid moieties at the sn-1 and sn-3 positions are oleic acid moieties;
at least 6%, preferably 6-17%, of said unsaturated fatty acid moieties at the sn-1 and sn-3 positions are linoleic acid moieties.

InFat is designed to have the right amount of palmitic acid and at the correct position of the triglycerides. The unique composition and structure of InFat mimics the fat composition and properties of human breast milk fat, and when incorporated in infant nutrition, offers exceptional nutritional and developmental benefits for infants and babies. This fat ensures optimal intake of calcium and also energy, in the form of free fatty acids.

In another aspect, the present invention provides a substitute human milk fat composition comprising a blend of at least 25% of the fat base composition of the invention, with up to 75% of at least one vegetable oil. This means that the fat base composition of the invention may be used to prepare a blend of substitute human milk fat, at a ratio of 1 part of the fat base composition to 3 parts of one or a combination of vegetable oil/s. In the following Examples, five blends are presented, InFat 1, InFat 2, InFat 3, InFat 4 and InFat 5, wherein different amounts of the fat base composition (InFat) were used, from 30% up to 83% of the content of the blend.

Thus, the present invention also provides a dietary ingredient comprising an edible lipid, wherein said edible lipid is a mimetic substitute of human breast milk fat.

InFat is designed to be blended with other complementary oils in order to achieve the final specified fatty acids composition of the infant formula. The right amount of palmitic acid, which is designed according to the structure and properties of human breast milk fat, offers not just better nutrition for infants but also greater flexibility when blending with complementary oils.

In this manner, the substitute human milk fat composition, i.e. the blend, may be prepared with any one or a combination of, for example, the following vegetable oils: soy, palm tree, canola, coconut, palm kernel, sunflower, corn and rapeseed oil, as well as other vegetable oils and fat.

Most importantly, the substitute human milk fat composition may be used in the preparation of infant formula.

Hence, in a further aspect, the present invention provides an infant formula, comprising the substitute human milk fat composition as described above. The infant formula provided by the invention is comprised of at least one protein component and at least one fat component, wherein said fat component is the substitute human milk fat composition as described above, and further optionally comprises vitamins, minerals, nucleotides, amino acids and carbohydrates.

In a yet further aspect, the present invention provides a process for the preparation of the fat base composition of the invention, comprising the steps of:
(a) reacting a palmitic acid rich oil with unsaturated fatty acids, preferably oleic acid, in the presence of an insoluble catalyst;
(b) removing the catalyst;
(c) distilling the excess free fatty acids;
(d) bleaching the oil; and
(e) optionally deodorizing the resulting composition.

This reaction is carried out at temperatures of preferably between 50° C. and 60° C.

In order to enhance the quality of the fat base, an optional further step of fractionation may precede the deodorization step (e).

The enzyme used in the above method is a 1,3 regiospecific lipase, which is preferably immobilized and surfactant coated. This enzyme preparation can be prepared according to the technology developed by the present inventors, and described in WO99/15689.

In EP 0 209 327 referred to above, for example, the process for preparing the fat composition involves the use of hexane, and a further step for its removal An important advantage of the process described herein is that it does not involve the use of solvents, which may leave potential toxic residues in the fat composition to be used in the preparation of infant formulas. Thus, the process of the invention yields a safer product.

In yet another aspect, the present invention provides a process for the preparation of the substitute human milk fat composition of as described herein, comprising admixing a vegetable oil or combination of oils with the fat-base composition of the invention. As mentioned above, several vegetable oils may be used for preparing the composition, including soybean oil, palm tree oil, canola oil, coconut oil, palm kernel oil, sunflower oil, corn oil and rapeseed oil.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example 1

Preparation of InFat

Specifically, InFat is an oil containing over 90% triglycerides. InFat also contains diglycerides. In some formulations, InFat can include up to 3% free fatty acids. The triglycerides of this product are characterized by a high percentage of palmitic acid at the sn-2 position, over 60%, preferably over 65% of the total palmitic acid in this oil. The sn-1 and 3 positions are characterized by a high percent of oleic acid and other unsaturated fatty acids.

InFat is produced by reacting a mixture of triglycerides, rich in palmitic acid, preferably above 78%, with a mixture of free fatty acids rich in oleic acid, preferably above 75%, with a low content of palmitic and stearic acids, preferably below 6%.

Preferably, the triglyceride mixture is produced from double-fractioned palm stearin and the free fatty acids (FFA) mixture is obtained from palm kernel oil after fractionation, or from high oleic sunflower oil. The ratio between triglycerides and FFA is from about 1:1 to about 1:10, particularly 1:4. The two mixtures are blended in stirred (optionally large scale) reactors with no additional solvent. To this mixture is added a surfactant coated immobilized 1,3-lipase (prepared as described in Applicant's WO00/56869), using an insoluble ion exchange resin for the immobilization and a suitable 1,3 lipases as described in said WO00/56869, preferably Rhizopus oryzae lipase. The mixture of triglycerides, FFA and catalyst is stirred at 50-60° C. for about 3-9 hours, to yield the final and desired triglycerides mixture. Progress and endpoint are monitored by positional analysis of triglycerides. The final process mixture is separated from the catalyst by decantation or filtration and the mixture of triglycerides and excess FFA are distilled to remove the FFA. FFA removal can be achieved, inter alia, by steam stripping or by molecular distillation. The distilled FFA are contaminated with palmitic acid, released from the triglyceride raw material during the reaction. The FFA can be purified from the excess palmitic acid in order to be reused in the reaction stage by several processes including selective dry fractionation, or fractional distillation. The triglyceride product is further treated in order to improve color, odor and taste with bleaching and deodrization stages. Optionally, the product is fortified with natural antioxidants to increase the shelf life of the product. The catalyst can be further recycled, to be re-used in further batches. A single catalyst preparation can be used for more than 100 batches (ratio of about 1:2 catalyst:triglycerides in the batch) and 1MT of catalyst is enough to produce more then 200 MT of final product. The product can be also produced by using a fixed bed reactor and a continuous process.

The following Table 1 details the contents of the resulting fat base composition of the invention (InFat), also referred to as "the concentrate material".

Example 2

Preparation of InFat Blends

InFat1 blend: InFat1 blend was produced by mixing several vegetable oils to a final fatty acid composition and palmitic acid positional distribution according to the specification below. The required vegetable oils and fats (all formulation components except the InFat) are mixed together and optionally are randomized to obtain 33% of the palmitic acid esterified in the $2^{nd}$ position. Afterwards, the interesterified blend is simply mixed with the InFat in the selected ratio. For InFat1 blend the following were used: 30% InFat concentrate (see Table 1 for fatty acid composition), 23% Coconut oil, 21% Palm oil, 10% Corn oil, and 16% Rapeseed oil. All vegetable oils used are standard food grade oils.

Thus, this blend is achieved with only 30% of InFat (the concentrate material). The ratio of sn-2:total palmitic acid is approximately 48.7%, and total palmitic acid is 22.8%. Even this blend, the simplest of blends presented herein, and containing only 30% of the InFat concentrate, is superior to available commercial HMF equivalent (approx. 43% ratio).

InFat2 blend: This blend was prepared in a similar manner, using 50% InFat concentrate (see Table 1 for fatty acid composition), 15% Coconut oil, 15% Palm oil, 5% Sunflower oil, 10% Corn oil, and 5% Rapeseed oil. All vegetable oils used are standard food grade oils.

Thus, this blend uses 50% of InFat™. The ratio of sn-2: total palmitic acid is approximately 56.3% and total palmitic content of 25.4% (25.7% in HMF) (this is superior to the ratio obtained with a similar percentage of available commercial HMF equivalent (approx. 52.5% ratio)).

InFat3 blend: This blend was prepared in a similar manner, using 63% InFat concentrate (see Table 1 for fatty acid composition), 16% Coconut oil, 9% Palm oil, and 12% Corn oil. All vegetable oils used are standard food grade oils.

The total palmitic acid is closer to breast milk, while only 63% of InFat were introduced. The ratio of sn-2:total palmitic acid is approximately 60.6%.

InFat4 blend: This blend was prepared in a similar manner, using 73% InFat concentrate (see Table 1 for fatty acid composition), 13.5% Coconut oil and 13.5% Rapeseed oil. All vegetable oils used are standard food grade oils.

This blend uses 73% of InFat™. The ratio of sn-2:total palmitic acid is approximately 67.4%, and total palmitic acid content is 25.1% (this is superior to the ratio obtained with a similar percentage of available commercial HMF equivalent (approx. 62.3 or 62.7% ratio)).

InFat5 blend: This blend was prepared in a similar manner, using 83% InFat concentrate (see Table 1 for fatty acid composition), 9.3% Coconut oil and 7.7% Sunflower oil. All vegetable oils used are standard food grade oils.

This is a very superior blend, in that it is similar to breast milk in the ratio of sn-2:total palmitic acid (68.5% vs. ~70% in IMF), total C16:0 (27.7% vs ~26% in HMF) and sn-2 C16:0 (56.9% vs. 57% in HMF).

The compositions of these five blends (InFat1, InFat 2, InFat 3, InFat 4, and InFat 5) are also given in Table 1.

TABLE 1

| Fatty acid | InFat | InFat 1 | InFat 2 | InFat 3 | InFat 4 | InFat 5 | Milk Fat |
|---|---|---|---|---|---|---|---|
| C12 |  | 11.1 | 7.2 | 7.8 | 6.5 | 4.4 | 2.3 |
| C14 |  | 4.5 | 3.1 | 3.3 | 2.8 | 2.1 | 5 |
| C16 | 32 | 22.8 | 25.4 | 26.9 | 25.1 | 27.7 | 25.7 |
| 2nd C16 | 67.2 | 33.4 | 42.9 | 48.9 | 50.8 | 56.9 | 57.5 |
| ratio | 70.0 | 48.7 | 56.3 | 60.7 | 67.4 | 68.5 | 74.6 |
| C16:1 |  |  |  |  |  |  |  |
| C18 | 4 | 2.3 | 3.0 | 3.1 | 3.5 | 4.0 | 7.1 |
| C18:1 | 53.1 | 38.4 | 40.8 | 41.6 | 47.9 | 46.6 | 38.5 |
| C18:2 | 8 | 13.5 | 15.6 | 12.8 | 8.6 | 11.7 | 11.7 |
| C18:3 |  | 1.7 | 0.6 |  |  |  |  |
| % concentrate | 100 | 30 | 50 | 63 | 73 | 83 |  |
| Coconut oil |  | 23 | 15 | 16 | 13.5 | 9.3 |  |
| Palm Kernel Oil |  |  |  |  |  |  |  |
| Palm oil |  | 21 | 15 | 9 |  |  |  |
| Sunflower |  |  | 5 |  |  | 7.7 |  |
| Corn oil |  | 10 | 10 | 12 |  |  |  |
| Rapeseed |  | 16 | 5 |  | 13.5 |  |  |
| Soybean |  |  |  |  |  |  |  |
| Total | 100 | 100 | 100 | 100 | 100 | 100 |  |

The table shows the fatty acid composition of the InFat concentrate and the InFat blends 1-5 as compared to HMF. C16 represents the total palmitic acid content. $2^{nd}$ C16 represents the % palmitic acid of total sn-2 position fatty acids. The ratio means the % of sn-2 palmitic acid of total palmitic acid normalized per position {(% of sn-2 palmitic)/(3× % total palmitic acid)}×100. All numbers represent % (w/w), except the ratio which is defined as %.

Example 3

Comparison of InFat Blends to Commercially Available Fat Concentrates

Table 2 is a comparison of InFat blends described in Example 2 to commercially available HMF mimetic preparations. In particular, it is important to compare the composition of InFat (the concentrate, Table 1) with that of the two commercially available concentrates (Concentrates 1 and 2, Table 2), and to compare the various InFat blends (InFat1-5, Table 1) with Blends 1-4 of the commercial concentrates (Table 2).

Comparison of the two concentrates of Table 2 with the InFat concentrate of Table 1 reveals that InFat has lower palmitic acid content which is closer to HMF, the sn-2 palmitic acid level is also lower and closer to HMF, and the ratio is higher and closer to the ratio in HMF. It should be noted that the concentrates are not usually used "as is" in infant formulas, since they do not contain other fatty acids required for the infant nutrition such as medium and short chain fatty acids, as well as LC-PUFA, such as Omega-3 DHA and Omega-6 ARA. The incorporation of such fatty acids is obtained by different blends.

As already described above, the blends of InFat are also superior to the blends of Table 2 in terms of mimicking HMF as well as in the proportions of the concentrate needed to obtain each blend, keeping in mind that the concentrate, being a synthetic oil, is the major-cost component of the blend and hence should be kept to a minimum in order to achieve cost effectiveness of such a nutrition product.

As described above, InFat2 can be compared to blend 2, which also utilizes a 50% concentrate. In InFat2 the ratio of sn-2:total palmitic acid is approximately 56.3% (57.5% in MF) and total palmitic content of 25.4% (25.7% in HMF). Blend 2 of Table 2 also uses 50% of concentrate but an inferior ratio of only 52.5% is obtained. Furthermore, in both total palmitic and sn-2 palmitic, InFat has some advantage in terms of similarity to HMF.

InFat3 blend has a ratio similar to blends 1, 3 and 4 of Table 2 but utilizes only 63% of concentrate, while these blends of Table 2 utilize 70%. InFat3 is also superior in terms of total palmitic acid which is closer to HMF.

InFat4, which is based on 73% InFat concentrate, can be compared to blends 1, 3 and 4 of Table 2, which are all also based on 70% of a commercial concentrate. In InFat4, the ratio of sn-2:total palmitic acid is approximately 67.4%, and total palmitic acid content is 25.1%, both values in good accord with HMF. Blends 3 and 4 of Table 2 have ratios of 62.8% and 62.3%, inferior to the present example, and a total of 30% or 30.5% palmitic acid, which is higher than in HMF.

InFat5 of course is superior and is not met by any of the blends described in Table 2.

Example 4

Infant Formula Based on InFat

An infant formula comprising InFat and additional oils and fats that mimic the human breast milk fat composition is prepared as follows: required oil blend is prepared by mixing of a selected formulation (e.g. those of Table 1). The oil is mixed together with the other infant formula components (proteins, carbohydrates, minerals, vitamins and others). The slurry is passed through a pressure homogenizer to get a stable emulsion. Homogenized product is then dried in a spray drier to obtain the final product. Other additives may be added to the dry powder to obtain final formulation.

The fat fraction produced by the blending of InFat with other oils and fats as described above is further blended with other nutrients such as proteins, minerals, vitamins and carbohydrates to yield a food product supplying the infant with the major nutrients also found in human milk. The nutrients and fats are homogenized using pressure homogenization and spray dried to yield a homogenous powder. The powder is further re-dispersed in water (approx. 9 g powder per 60 ml water) to yield a ready-to-feed formula. The fat content of the ready feed is approx. 3.5 g per 100 ml which corresponds to the fat content of human breast milk, which is in the range of 30-40 g/L.

The fatty acid composition of a blend of InFat (30%) with other oils and fats used to create an infant formula is as follows:

| Fatty acid | % |
|---|---|
| C10:0 | 1.3 |
| C12:0 | 10.3 |
| C14:0 | 4.3 |
| C16:0 | 23.5 |
| sn-2 C16:0 (% of total C16:0) | 43 |
| C18:0 | 3.2 |
| C18:1 | 39.2 |
| C18:2 | 13.6 |

TABLE 2

| | Blend 1 | Blend 2 | Blend 3 | Blend 4 | Concentrate 1 | Concentrate 2 | Milk Fat |
|---|---|---|---|---|---|---|---|
| C12 | 9.5 | 5 | 5 | 10 | | | 2.3 |
| C14 | 3 | 2 | 1.5 | 3 | | | 5 |
| C16 | 33 | 26 | 30 | 30.5 | 44.5 | 40 | 25.7 |
| 2nd C16 | 57 | 41 | 56.5 | 57 | 80 | 80 | 57.5 |
| Ratio | 57.6 | 52.6 | 62.8 | 62.3 | 59.9 | 66.7 | 74.6 |
| C16:1 | 2 | 1.5 | | 2.5 | 3.5 | 3.5 | 5.1 |
| C18 | 5.5 | 5 | 1 | 5 | 6 | 6.5 | 7.1 |
| C18:1 | 35 | 33.5 | 47.5 | 36.5 | 41.5 | 44.5 | 38.5 |
| C18:2 | 10.5 | 23 | 15 | 10.5 | 4.5 | 5.5 | 11.7 |
| C18:3 | | | | | | | |
| % concentrate | 70 | 50 | 70 | 70 | 100 | 100 | |
| Coconut oil | | | | | | | |
| Palm Kernel Oil | 20 | 10 | 10 | 20 | | | |
| Palm oil | | | | | | | |
| Sunflower | 10 | 10 | 20 | 10 | | | |
| Corn oil | | | | | | | |
| Rapeseed | | | | | | | |
| Soybean | | 30 | | | | | |
| Total | 100 | 100 | 100 | 100 | 100 | 100 | 0 |

-continued

| | |
|---|---|
| C18:3 | 1.7 |
| C20:0 | 0.3 |
| C20:1 | 0.3 |
| C22:0 | 0.2 |

| | per 100 g powder | Per 100 ml ready to feed |
|---|---|---|
| Energy kcal | 508 | 68 |
| Sodium mg | 140 | 18.8 |
| Protein g Lacatalbumin/Casein 60/40) | 11.4 | 1.5 |
| Fat g | 26.5 | 3.5 |
| Saturated fat g | 14.5 | 1.95 |
| Linoleic acid | 5000 | 670 |
| Alpha-linolenic acid mg | 530 | 71 |
| Arachidonic acid mg | 115 | 15.3 |
| Docosahexaenoic acid mg | 108 | 14.4 |
| Cholesterol mg | 2 | 0.3 |
| Lactose g | 56 | 7.5 |
| Calcium mg | 430 | 57.3 |
| Phosphorus mg | 250 | 33.5 |
| Potassium mg | 420 | 56.3 |
| Chloride mg | 300 | 40.2 |
| Iron mg | 5.25 | 0.7 |
| Magnesium mg | 50 | 6.7 |
| Zinc mg | 3.5 | 0.47 |
| Copper mcg | 300 | 40.2 |
| Manganese mcg | 45 | 6 |
| Iodine mcg | 45 | 6 |
| Taurine mg | 45 | 6 |
| Vitamin A I.U. | 1500 | 200 |
| Vitamin D I.U. | 300 | 40.2 |
| Vitamin E mg | 10 | 1.3 |
| Vitamin K mcg | 45 | 6 |
| Vitamin C mg | 60 | 8 |
| Vitamin $B_1$ mcg | 400 | 53 |
| Vitamin $B_2$ mcg | 800 | 127 |
| Vitamin $B_6$ mcg | 375 | 50 |
| Vitamin $B_{12}$ mcg | 1.15 | 0.2 |
| Niacin mg | 6 | 0.8 |
| Panthothenic acid mg | 3 | 0.4 |
| Folic acid mcg | 67 | 9 |
| Biotin mcg | 14.3 | 1.9 |
| Choline mg | 37.5 | 5 |
| Inositol mg | 22.5 | 3 |
| Moisture % | 3 | |

The level of fat and the exact composition can be controlled in order to yield infant formulas designed to mimic the different lactation periods.

The invention claimed is:

1. A substitute milk fat composition comprising a blend of at least 25% to 50% of an edible, synthetic fat base mixed with from 50% to 75% of at least one enzymatically-randomized vegetable oil, wherein the edible, synthetic fat base is a mixture of processed vegetable oils, wherein the fat base is enzymatically-prepared; and wherein over 90% of the fat base is a mixture of processed vegetable oil triglycerides in which mixture:
 the total palmitic acid residues content is not more than 38% w/w of the total fatty acid residues of the triglycerides;
 from 62% to 70% of the total palmitic acid residues of the triglycerides are attached at the sn-2 position of the glycerol backbone of the triglycerides;
 at least 60% w/w of the fatty acid residues attached at the sn-2 position of the glycerol backbone of the triglycerides are palmitic acid residues;
 at least 70% w/w of the fatty acid residues attached at the sn-1 and sn-3 positions of the glycerol backbone of the triglycerides are unsaturated fatty acid residues;
 from 6-17% w/w of the unsaturated fatty acid residues at the sn-1 and sn-3 positions of the glycerol backbone of the triglycerides are linoleic acid residues; and
 from 40-60% w/w of the unsaturated fatty acid residues at the sn-1 and sn-3 positions of the glycerol backbone of the triglycerides are oleic acid residues.

2. The substitute milk fat composition of claim 1, wherein the at least one enzymatically-randomized vegetable oil is selected from the group consisting of soy oil, canola oil, coconut oil, palm kernel oil, sunflower oil, corn oil, rapeseed oil, and mixtures thereof.

3. An infant formula comprising the substitute milk fat composition of claim 1.

4. An infant formula comprising at least one protein component and at least one fat component, wherein the fat component is the substitute milk fat composition of claim 1 and the infant formula further comprises at least one of a vitamin, a mineral, a nucleotide, an amino acid, and a carbohydrate.

5. The substitute milk fat composition according to claim 1, wherein the triglycerides content of palmitic fatty acid residues is 32% w/w, the triglycerides content of oleic fatty acid residues is 53.1% w/w, the triglycerides content of linoleic fatty acid residues is 8% w/w, and wherein the synthetic fat base composition further comprises a triglycerides content of stearic fatty acid residues of 4% w/w.

6. A substitute human milk fat composition comprising a blend of at least 25% to 50% of a fat base composition which fat base composition comprises a mixture of processed vegetable oils, with from 50% to 75% of at least one enzymatically-randomized vegetable oil, wherein the fat base composition is produced by reacting a palmitic acid-rich vegetable oil comprising above 78% palmitic acid residues with unsaturated fatty acids comprising above 75% oleic acid residues in the presence of an insoluble catalyst, removing the catalyst, and distilling any free fatty acids,
 wherein over 90% of the fat base composition are a mixture of triglycerides in which mixture:
 the total palmitic acid residues content is not more than 38% w/w of total fatty acid residues of the triglycerides;
 from 62% to 70% w/w of total palmitic acid residues of the triglycerides are attached at the sn-2 position of glycerol backbone of the triglycerides;
 at least 60% w/w of fatty acid residues attached at the sn-2 position of the glycerol backbone of the triglycerides are palmitic acid residues;
 at least 70% w/w of fatty acid residues attached at the sn-1 and sn-3 positions of the glycerol backbone of the triglycerides are unsaturated fatty acid residues;
 from 6 to 17% w/w of unsaturated fatty acid residues at the sn-1 and sn-3 positions of the glycerol backbone of the triglycerides are linoleic acid residues; and
 from 40 to 60% w/w of unsaturated fatty acid residues at the sn-1 and sn-3 positions of the glycerol backbone of the triglycerides are oleic acid residues; and
 wherein the blend is prepared by admixing the fat base composition with the at least one enzymatically-randomized vegetable oil, and in which blend:
 from 22 to 33% w/w of total fatty acid residues are palmitic acid residues;
 from 33 to 57% w/w of fatty acid residues attached at an sn-2 position of the glycerol backbone of the triglycerides are palmitic acid residues;
 from 48 to 69% w/w of the total palmitic acid residues of the triglycerides are attached at the sn-2 position of the glycerol backbone of the triglycerides;
 from 33 to 48% w/w of fatty acid residues are oleic acid residues; and from 8 to 23% w/w of fatty acid residues are linoleic acid residues.

7. A process for preparation of a substitute human milk fat composition, the process comprising admixing an enzymatically-randomized vegetable oil selected from the group consisting of soy oil, canola oil, coconut oil, palm kernel oil, sunflower oil, corn oil, rapeseed oil, and mixtures thereof with an edible, synthetic fat base composition, wherein the edible, synthetic fat base composition is a mixture of processed vegetable oils, wherein the fat base is enzymatically-prepared; and wherein over 90% of the composition a mixture of processed vegetable oil triglycerides in which mixture:

the total palmitic acid residues content is not more than 38% w/w of the total fatty acid residues of the triglycerides;

from 62% to 70% of the total palmitic acid residues of the triglycerides are attached at the sn-2 position of the glycerol backbone of the triglycerides;

at least 60% w/w of the fatty acid residues attached at the sn-2 position of the glycerol backbone of the triglycerides are palmitic acid residues;

at least 70% w/w of the fatty acid residues attached at the sn-1 and sn-3 positions of the glycerol backbone of the triglycerides are unsaturated fatty acid residues;

from 6-17% w/w of the unsaturated fatty acid residues at the sn-1 and sn-3 positions of the glycerol backbone of the triglycerides are linoleic acid residues; and from 40-60% w/w of the unsaturated fatty acid residues at the sn-1 and sn-3 positions of the glycerol backbone of the triglycerides are oleic acid residues.

8. A process for preparation of an infant formula, the process comprising blending at least 25% to 50% of an edible, synthetic fat base composition with from 50% to 75% of an enzymatically-randomized vegetable oil selected from the group consisting of soy oil, canola oil, coconut oil, palm kernel oil, sunflower oil, corn oil, rapeseed oil, and mixtures thereof; and mixing the blend with at least one protein component and at least one of carbohydrates, vitamins, and minerals; wherein the edible, synthetic fat base composition is a mixture of processed vegetable oils, wherein the fat base is enzymatically-prepared; and wherein over 90% of the composition is a mixture of processed vegetable oil triglycerides in which mixture:

the total palmitic acid residues content is not more than 38% w/w of the total fatty acid residues of the triglycerides;

from 62% to 70% of the total palmitic acid residues of the triglycerides are attached at the sn-2 position of the glycerol backbone of the triglycerides;

at least 60% w/w of the fatty acid residues attached at the sn-2 position of the glycerol backbone of the triglycerides are palmitic acid residues;

at least 70% w/w of the fatty acid residues attached at the sn-1 and sn-3 positions of the glycerol backbone of the triglycerides are unsaturated fatty acid residues;

from 6-17% w/w of the unsaturated fatty acid residues at the sn-1 and sn-3 positions of the glycerol backbone of the triglycerides are linoleic acid residues; and from 40-60% w/w of the unsaturated fatty acid residues at the sn-1 and sn-3 positions of the glycerol backbone of the triglycerides are oleic acid residues.

* * * * *